Figure 1:
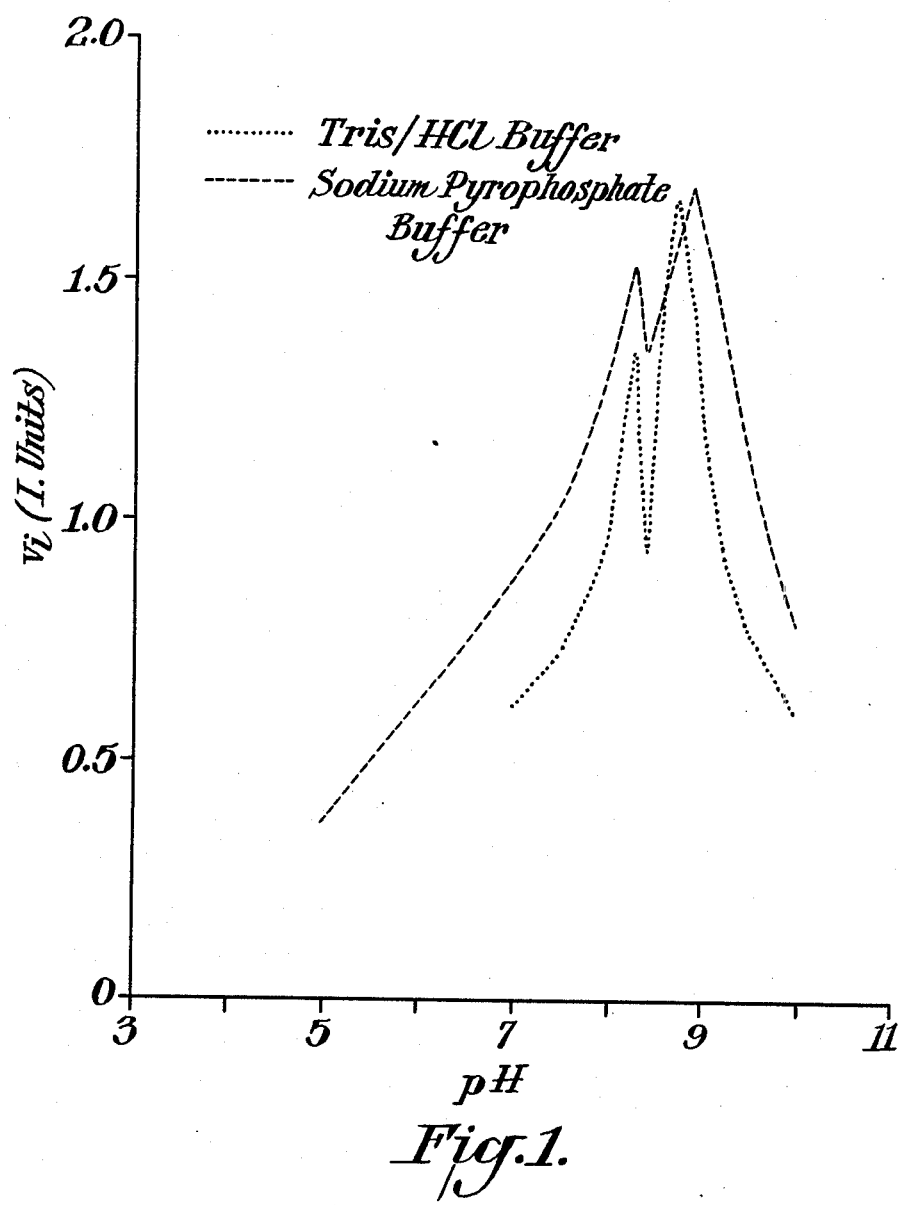

United States Patent [19]

Zikakis

[11] 4,238,566
[45] Dec. 9, 1980

[54] XANTHINE OXIDASE

[75] Inventor: John P. Zikakis, Townsend, Del.

[73] Assignee: University of Delaware, Newark, Del.

[21] Appl. No.: 114,047

[22] Filed: Jan. 21, 1980

Related U.S. Application Data

[60] Continuation-in-part of Ser. No. 14,338, Feb. 23, 1979, abandoned, which is a division of Ser. No. 806,736, Jun. 15, 1977, Pat. No. 4,172,763.

[51] Int. Cl.$^3$ .......................... C12N 9/02; C12N 9/06
[52] U.S. Cl. ..................................... 435/189; 435/191
[58] Field of Search ................................ 435/189, 191

[56] References Cited

PUBLICATIONS

Waud et al., Archives of Biochemistry and Biophysics, vol. 169, pp. 695–701 (1975).
Methods in Enzymology, vol. II, 1955, pp. 482–485.

*Primary Examiner*—Lionel M. Shapiro

[57] ABSTRACT

A milk xanthine oxidase active enzyme concentrate having an average protein to flavin ratio as measured by $E_{280nm}$ for protein and $E_{450nm}$ for flavin of 2.0 to 4.1, one symmetric peak by ion-exchange gel chromatography, and shows a single protein band by polyacrylamide disc gel electrophoresis. The xanthine oxidase is not denatured.

2 Claims, 2 Drawing Figures

XANTHINE OXIDASE

This application is a continuation in part of application Ser. No. 014338 filed Feb. 23, 1979, now abandoned, which was a division of application Ser. No. 806736 filed June 15, 1977, now U.S. Pat. No. 4,172,763 dated Oct. 30, 1979.

FIELD OF THE INVENTION

This invention relates to a new and improved xanthine oxidase (referred to herein as XO) concentrate from bovine milk.

Prior Art

Bovine milk xanthine oxidase (xanthine: oxygen oxidoreductase, E.C. 1.2.3.2.) is a conjugated iron-sulfur molybdenum flavoprotein widely distributed in animals, plants, and microorganisms where it has a role in purine catabolism. In many animals, including primates, XO is found in the liver, kidney, blood, intestinal mucosa and milk (Li and Vallee, In Modern Nutrition in Health and Disease: Dietotherapy, 5th Ed. Lea and Febiger, Philadelphia, Pa., pp. 372-399, 1973; Zikakis et al, J. Food Sci. 41:1408-1412, 1976). It catalyzes uric acid production from hypoxanthine and xanthine in terminal purine catabolism.

Most of the XO in cow's milk is closely associated with the milk fat globule membrane (MFGM) (Morton, Biochem J. 57:231-237, 1954). The MFGM has a protenaceous surface that interfaces with the milk plasma phase on the exterior and the globule lipids on the interior (Brunner, In Fundamentals of Dairy Chemistry, 2nd Ed. AVI Publishing Co., Westport, Conn., pp. 474-602, 1974).

Ball in 1939 (J. Biol. Chem. 128:51-67) was the first to attempt to isolate and partially purify XO from cow's milk by treating buttermilk with pancreatin. From 1955 to the recent past, numerous purification methods for cow's milk XO have been described. Pancreatin has been used in XO purification to degrade casein micelles to lower molecular weight components so that they may be eluted behind XO in subsequent chromatographic fractionations. However, pancreatin is not specific for casein degradation, and has a proteolytic effect on all proteins (Nelson and Handler, J. Biol. Chem. 243:5368-73, 1968). Avis et al., (J. Chem. Soc. (London) pp. 1100-1105, 1955) managed to crystallize XO in the presence of ethanol giving a protein/flavin ratio (a most important purity index for XO) of 5.0-5.2. However, the yield was poor and the specific activity of the product varied widely.

Horecker and Heppel in an article published in Methods in Enzymology, Vol. II, 1955, pages 482-485, describe a process for the concentration and purification of XO from cow's milk by five steps, the first two following the procedure of Ball but using Trypsin for digestion followed by the steps of (3) ammonium sulfate fractionation; (4) aluminum hydroxide gel absorption and elution; and (5) calcium phosphate gel absorption and elution. The detailed process of Horecker and Heppel has been repeated with the results indicated and produces a XO concentrate that has a $E_{280}/E_{450}$, protein/flavin ratio of 6.1.

In 1964, Gilbert and Bergel (Biochem. J. 90:350-353) published a method which improved the yield but the product was less pure ($E_{280}/E_{450}$ ranged from 5.4-6.0) than that of Avis et al., 1955. Their method included pancreatin digestion of the buttermilk, treatment with butanol, and the addition of EDTA and sodium salicylate. In 1968 Nelson and Handler prepared milk XO by a non-proteolytic method (i.e., without pancreatin digestion). They concluded that their preparation was homogeneous, with a $E_{280}/E_{450}$ ratio of 5.1-5.3. Hart et al., (Biochem. J. 116:851-863, 1970) and Nelson and Handler (1968) have indicated that purified XO differs according to the purification method, and that proteolysis adversely affects the enzyme. Waud et al. (Arch. Biochem. Biophys. 169:695-701, 1975), and Nagler and Vartanyan (Biochem. Biophys. Acta 427:78-90, 1976) demonstrated that purification procedures employing pancreatin yield XO and sub-units with lower molecular weight, and that the XO migrates faster on polyacrylamide gel electrophoresis that XO prepared by a non-proteolytic treatment. Furthermore, Nathans and Hade (Biochem. Biophys. Res. Comm. 66:108-114, 1975) showed that XO isolated in the presence of pancreatin copurifies with proteases from pancreatin. The non-proteolytic procedure of Waud et al., (1975) which comprises butanol extraction, ammonium sulfate precipitation, and chromatography is the best available method. The final product never has a $E_{280}/E_{450}$ ratio (or as referred to in the article $A_{280nm}:A_{450nm}$) better than 4.8 and the yield is 10%.

The most sensitive indicator of XO purity is the PFR ($E_{280}/E_{450}$) value (Hart et al., 1970). A decrease in the concentration of non-XO protein (at 280 nm) and a simultaneous increase in the concentration of XO (at 450 nm) should give an increasingly lower $E_{280}/E_{450}$ ratio. Thus, the lower the PFR value, the higher the purity of the preparation. PFR values obtained by various methods are: 6.2 (Corran et al., 1939), 6.2 (Morell. Biochem. J. 51:657-666, 1952), 5.0 (Avis et al., 1955), 6.1 (Horecker and Heppel, 1955), 5.4 (Gilbert and Bergel, 1964), 5.1 (Nelson and Handler, 1968), 5.2 (Nagler and Vartanyan, 1973), and 4.8 (Waud et al., 1975).

In summary, prior art teaches an incubation of milk buffered with Sodium Salicylate and EDTA; digestion with pancreatin, or extraction with butanol, washing with an ionic detergent; precipitation of casein with ammonium sulfate; further removal of casein by treatment with ammonium sulfate, and finally purifying on one or two chromatographic columns.

The objective of this invention is to obtain an improved XO concentrate as compared to the XO concentrate produced by prior art. This object is accomplished by the use of the following process, which process is also described and claimed in inventor's U.S. Pat. No. 4,172,763 granted Oct. 30, 1979.

The obtaining of an improved XO concentrate involves the following isolation and purification of XO from bovine raw milk. To assure good yield, the starting milk is assayed for XO activity before using it. As a rule, good yield is expected when the activity of starting fresh raw milk (which is maintained immediately after milking at 38° C. and assayed within 60 min.) is above 60 $\mu$l $O_2$/ml/hr. or above 140 $\mu$l $O_2$/ml/hr. for raw milk kept at 4° C. for 1-12 hrs. after milking. Sodium salicylate and EDTA are added as enzyme protectors. The mixture is diluted 1:1 with potassium phosphate buffer and incubated at 40° to 45° C. for 2 hours with continuous mixing. After 105 min. of incubation, 1% by volume of Triton X-100 or a similar non-ionic detergent is added and the mixture is allowed to incubate for the remaining 15 min. The use of a non-ionic detergent facilitates the separation of the XO from MFGM without adding ionic salts or degrading the enzyme.

The mixture is cooled to 4° C. and all subsequent steps are carried at that temperature. Solid ammonium sulfate is added (200 gm/liter) to the mixture, which is stirred for 15 min., and then centrifuged at 12,225 g for 20 min. To the resulting yellow supernatant liquid, which contained the enzyme, solid ammonium sulfate is added (70 gm/liter), stirred for 15 min., and centrifuged at 12,225 g for 20 min. The red-brown percipitate is dissolved in a minimal volume of 0.1 M Tris*/CaCL$_2$ buffer (pH 7.0) and stored at freezing or below (e.g. $-20°$ C.) for from 0.5 to 7.0 days. Prior art does not call for storage at that temperature, but this step precipitates caseins which are the commonest non-XO proteins in milk.

*Tris(hydroxymethyl)aminomethane

The frozen preparation is thawed and centrifuged at 12,225 g for 20 min. The active enzyme retained in the supernatant liquid is concentrated on a XM50 microfilter and applied on a Sephadex G-75 column. The eluted fractions are analyzed spectrophotemetrically at 280 and 450 nm and catalytic activity is measured at 295 nm. Fractions showing activity are pooled, concentrated, and reanalyzed as above. The concentrated sample is applied on a Sephacryl S-200 superfine or on a Sephadex G-200 column. The eluted fractions are analyzed for absorption and activity, active fractions pooled, concentrated as above, and passed through a Sepharose 6B type column. All eluted fractions are tested as above; fractions with activity are pooled, concentrated as above, and desalted by passed throgh a Sephadex G-75 column. Finally, the active fractions from this column are pooled, concentrated, and applied on either a DEAE Sephadex A-50 or on DEAE Sepharose CL-6B anionic exchange column and eluted in a continuous linear salt gradient from 0.005 to 0.1 M pyrophosphate buffer, pH 8.6.

The sizing of the ultrafiltration membrane and the order of use of the chromatographic columns are both important. According to the majority of studies, the M.W. of XO is about 300,000 daltons (Waud et al., 1975; Nagler and Vartanyan, (Biokhimiya 38:561–567, 1973—translated from Russian) with two subunits of about 150,000 daltons (Nathans and Hade, 1975; Nagler and Vartanyan, 1976). In turn, this subunit of XO may be a dimer of 80,000–85,000 daltons. This is supported by the fact that the ultrafiltrate of XO preparations passed through an Amicon XM-100A membrane (with a nominal cutoff of 100,000 daltons) contained active XO (Nathans and Hade, 1975; Biasotto and Zikakis (J. Dairy Sci. 58:1238, 1975). This suggests that XO may be a tetramer which may undergo dissociation and reassociation. Thus, to avoid the loss of monomers of XO and increase the yield, the Amicon XM-50 membrane (nominal cutoff 50,000 daltons) was used in this procedure. This membrane retains molecules with M.W. above 50,000 and allows all others to pass through. The first column used is Sephadex G-75 which retains salts and light particles and allows heavy particles (including XO) to come out first. Both Sepharyl S-200 and Sepharose 6B columns separate proteins in the preparation according to molecular size. Before the final purification step through DEAE Sephadex A-50 (or through DEAE Sepharose CL-6B) anionic exchange column, the XO preparation is passed again through Sephadex G-75 to remove all salts (this is a necessary step; otherwise, XO will not bind to the anionic exchange column).

The following example describes in greater detail the preferred process steps used in carrying out the process used to produce the new and improved XO concentrate.

EXAMPLE

1. To one liter of fresh raw milk (from the University of Delaware Guernsey herd) 10 ml of 200 mM sodium salicylate and 0.1 gm EDTA added and mixed. Sodium salicylate stabilizes XO while EDTA chelates heavy metal comtainants. One liter of 0.2 M potassium phosphate buffer (pH 7.8), containing 8 mM sodium salicylate and 4 mM cysteine-HCL, was added to the mixture and mixed. The final concentration of solutes in this 2 liter mixture was 5 mM sodium salicylate, 0.005% EDTA, 0.1 M K$_2$HPO$_4$, and 2 mM cysteine-HCL. The pH of the mixture ranged between 7.8 to 7.9.

2. The mixture was incubated while stirring at 40° to 45° C. for 2 hours. After 105 minutes incubation, 1% (V/V) Triton X-100 was added to the mixture and the mixture allowed to continue incubation for 15 minutes. Triton X-100 is a mild nonionic detergent which is effective in dissolving the MFGM. Triton X-100 is a substitute for the much harsher lipolytic enzymes (which may adversely effect the purity of XO) and butanol (which is a denaturant and a substance difficult to work with) presently used in other methods. At the end of the two-hour incubation, the mixture was cooled to 4° C. and, unless stated otherwise, all subsequent steps of the method were carried out at this temperature.

3. 400 gm of solid ammonium sulfate (20% W/V) was added to the mixture with stirring. The suspension was stirred for 15 minutes and then centrifuged at 12,225 g for 20 minutes in an International Refrigerated Centrifuged (Model B-20). Three distinct layers were formed after centrifugation. The upper layer (the milkfat) and the white precipitate (the caseins) at the bottom of the tubes were devoid of XO activity and were discarded. The supernatant liquid was passed through glass wool into a graduated cylinder. The filtrate was an opalescent yellow fluid which contained all the XO activity.

4. The concentration of ammonium sulfate in the filtered supernatant liquid was adjusted from 20% to 27% with solid ammonium sulfate, the mixture stirred for 15 minutes and centrifuged at 12,225 g for 20 min. The resultant browish-red precipitate was dissolved in 10 to 15 ml of 0.1 M Tris-HCl buffer (pH 7.0) containing 2 mM sodium salicylate and 0.07 M CaCl$_2$ and stored for at least 15 hours at $-20°$ C. The objective of this step was the precipitation of caseins (Ball 1939). About 80% of the total protein in cow's milk is casein which precipitates over the range of 20 to 26.4% (W/V) ammonium sulfate (McKenzie, In Milk Protein Chemistry and Molecular Biology, Vol. 2 pp. 87–114, Acad. Press, NY, NY, 1971). This fractionation range is close to the 27% (W/V) ammonium sulfate used to precipitate XO in this procedure. Therefore, the incusion of some caseins in the above precipitations is unavoidable.

5. Upon thawing the mixture to 22° C., it yielded a course white precipitate of caseins. Upon centrifugation at 12,225 g and 4° C. for 20 min., the mixture yielded a reddish-brown supernatant liquid and a slightly brown precipitate. The precipitate was redissolved in 0.1 M Tris/CaCl$_2$ buffer and recentrifuged. The supernatant liquid from both centrifugations was combined and showed high activity of XO, while the white pirecipitate of cesins had negligible activity. It was found that the longer the preparation was frozen, the more caseins can be removed. Maximum casein precipitation occurs after about 3 to 4 weeks of storage at −20° C. Therefore, the time of cold storage is a function of economics and the desired purity. The precipitation of casein is very slow after 7 days and some decomposition of XO will occur, even at −20° C. Storage of most batches were from 15 hours to 1 week, which is usually a satisfactory operating range.

6. The active reddish-brown supernatant obtained in step 5 was concentrated to 5 ml on an Amicon ultrafiltration system using a XM50 membrane designed to retain molecules of 50,000 daltons and greater. This concentrate was then applied on a Sephadex G-75 superfine column (1.5×125 cm), which has been equilibrated with 0.1 M pyrophosphate buffer pH 7.1, and the column was eluted with the same buffer. The purpose of this chromatographic step was to desalt (remove the ammonium sulfate) and remove low molecular weight (<75,000 daltons) impurities from the sample. All fractions were analyzed individually at 280 nm for protein and at 450 nm for flavin adenine dinucleotide (FAD) on either a Beckman DB or a Gilford Model 250 spectrophotometer. From this point on, the enzyme activity in each fraction was measured spectrophotometrically at 295 nm and 23.5° C. Fractions with activity were pooled and concentrated by ultrafiltration as above to 5 ml. The pooled sample was analyzed for activity, absorption spectra, total protein, and electrophoretic behavior.

7. The pooled, concentrated sample from step 6 was applied on a Sephacryl S-200 superfine or on a Sephadex G-200 column (2.5×100 cm) equilibrated with 0.1 M pyrophosphate buffer 7.1, and the column was eluted with the same buffer. All fractions wre analyzed as above. Fractions with no activity were discarded. The remaining fractions showed increases in purity as judged by the protein flavin rations (PFR), activity-flavin ratio (AFR), activity-protein ratio (APR), and electrophoresis.

8. The fractions from the Sephacryl S-200 (or the Sephadex G-200) (step 7) showing XO activity at 295 nm and flavin at 450 mn, were pooled, concentrated, and applied on a Sepharose 6B column (2.5×100 cm) equilibrated and eluted with 0.1 M phrophosphate buffer pH 7.1. Following analyses of eluted fractions, those with XO activity were pooled and concentrated to about 3 ml by ultrafiltration using a XM50 membrane.

9. The concentrated sample of step 8 was desalted by passing it through a Sephadex G-75 column (0.9×60 cm) equilibrated and eluted with a 0.005 M sodium pyrophosphate buffer pH 8.6. Fractions containing the enzyme were pooled and concentrated on a XM50 membrane.

10. The concentrated sample was applied on a DEAE Sephadex 50-A (or on a DEAE Sepharose CL-6B) anionic exchange column (1.6×20 cm) which was equilibrated with 0.005 M sodium pyrophosphate buffer pH 8.6. Initial elution of the column was with the 0.005 M phosphate buffer. At this pH and salt concentration, XO is effectively bound to the exchange as was apparent from the appearance of a dark brown band in the upper 2 to 4 cm of the column and its failure to elute in 0.005 M salt. Elution of XO from the column was accomplished on a linear continuous salt gradient from 0.005 M to 0.1 M sodium pyrophosphate pH 8.6. Typical data obtained at various stages of XO preparation are listed in Table b 1.

TABLE 1

TYPICAL DATE OBTAINED AT VARIOUS STAGES OF XANTHINE OXIDASE PURIFICATION FROM GUERNSEY MILK

| PROCEDURE | TOTAL VOLUME (ml) | ACTIVITY (I UNITS/ ml) | PROTEIN (mg/ml) | SPEC. ACTIVITY | PER[1] | PURIFICATION |
|---|---|---|---|---|---|---|
| WHOLE MILK | 1000 | 0.034* | 22.66 | 0.0015 | ** | 0 |
| AFTER BUFFER ADDITION | 2000 | 0.017* | 11.32 | 0.0015 | ** | 0 |
| AFTER DIGESTION | 2000 | 0.104* | 12.60 | 0.0083 | ** | 5.6 |
| 20% CUT | 1862 | 0.115* | 2.26 | 0.051 | ** | 34.0 |
| 7% CUT | 6.5 | 31.89 | 18.90 | 1.687 | 24.5 | 1125.0 |
| G-75 | 6.0 | 18.43 | 18.60 | 0.991 | 16.0 | 660.6 |
| SEPHACRYL S-200 OR SEPHADEX G-200 | 6.0 | 17.71 | 12.40 | 1.428 | 10.0 | 952.0 |
| SEPHAROSE 6B | 3.5 | 20.71 | 12.40 | 1.670 | 8.0 | 1113.3 |
| DEAE+ | 3.5 | 12.20 | 1.70 | 7.176 | 4.1 | 4784.3 |

[1]PROTEIN FLAVIN RATIO.
*ACTIVITY OF SAMPLES PRIOR TO THE 7% AMMONIUM SULFATE CUT WAS DETERMINED POLAROGRAPHICALLY.
**THE PFR COULD NOT BE CALCULATED FOR SAMPLES PRIOR TO THE 7% AMMONIUM SULFATE CUT DUE TO THE TURBIDITY OF THE SAMPLE.

The PFR value of the final XO concentrate prepared by repeating the above described method ranged from 2.7 to 4.8 and averaged 4.1. The yield of the method ranges from 18–26% and average 21%. Therefore, this method produces a XO concentrate which is on the average about 20% purer (about 4800 fold purified) and yields about 110% more XO than the best available method in literature (Waud et al., 1975).

More highly purified XO with PFR value approaching 2.0 can be obtained by this method using additional treatment in columns, but the yield is smaller and the cost of the product is greater.

In addition to a marked increase in purity and a higher yield, the XO active enzyme concentrate of this invention has one symmetric peak by ion-exchange chromatography, and its behavior on polyacrylamide disc gel electrophoresis showed a single protein band, stained with Coomassie Brilliant Blue. Comparative analyses of commercially available XO concentrate, and of XO concentrate of this invention, revealed that commercial XO concentrate migrates faster in electrophoresis than does XO concentrate of this invention. Furthermore, the commercial XO concentrate contained 7-14 protein bands, determined by staining with Coomassie Brilliant Blue, depending on the batch.

In addition to the differences noted, the following experimental work comparing the XO concentrate of this invention with the XO concentrate of the prior art processes shows marked characteristic differences that are more than a difference in degree of purity. These differences are set forth in Table 2. It is believed that the XO concentrate of this invention provides an active XO enzyme of a different molecular structure than that provided in the XO concentrate of the prior art.

Bovine milk XO was purified using three different methods and the purified XO enzyme concentrate preparation from each method was assayed for its kinetic parameters.

The first method used was that of Horecker and Heppel (Methods in Enzymology, Vol. 2, pp. 482–485, 1955). The XO concentrate obtained had an $E_{280}/E_{450}$ ratio of 6.1. The second method was that of Waud et al. (Arch. Biochem. and Biophys., Vol. 169, pp. 695–701, 1975). The XO concentrate obtained had an $E_{280}/E_{450}$ ratio of 4.8. The third method was that described above for the preparation of the XO concentrate of this invention. The XO concentrate had an average $E_{280}/E_{450}$ ratio ranging from 2.0 to 4.1.

The various procedures used to collect the kinetic data in Table 2 are as follows.

1. Determination of Temperature Optima.

The temperature optima for XO prepared by the 3 methods were determined using a Gilford 250 digital spectrophotometer equipped with an automatic cuvette positioner (for enzyme kinetics), a rapid sampler, a reference compensator, and a variable speed recorder. Constant temperature ($\pm 0.001°$ C.) within the environment of the cuvette chamber was maintained by a Forma Scientific refrigerated heated water bath circulator which was connected to the thermoplates of the cuvette positioner. For the assay, four matched one cm quartz cuvettes were used. The temperature of the reactants in the cuvettes was monitored by a digital thermometer (Cole Palmer Instrument Co., Model 8520).

The temperature assays were performed using 0.1 M pyrophosphate buffer, pH 8.7. Assay conditions were as follows: 2.5 ml of pyrophosphate buffer (maintained at approximately 75% saturation with oxygen) and 25 microliters of 10 mM xanthine (dissolved in 20 mM NaOH) were placed in cuvette and thoroughly mixed. This dilution gave a final xanthine concentration of $1.0 \times 10^{-4}$M. The assay mixture was allowed to reach thermal equilibrium in the spectrophotometer for 10 minutes prior to the initiation of the reaction. The XO preparation to be tested was removed from the refrigerated (4° C.) sample container and incubated in the cuvette chamber prior to the initiation of the reaction. The reaction was started by injecting with a microsyringe 15 microliters of the enzyme to be tested. Spectrophotometer sensitivityy was set at 0.1 Absorbance full scale and the chart speed at 2 cm/min. Three replicates of each assay were performed and temperatures were increased two degrees between each set of tests. All 3 XO preparations were assayed over the range of temperatures from 10° C. to 50° C. In the region of the temperature optimum, assays were performed every one degree for five degrees on either side of the optimum.

Each assay was allowed to run for seven minutes and initial velocities were determined from the slope of uric acid production (at 295 nm) curve within the first three minutes of the reaction. Plots were then constructed on the initial velocity versus temperature.

The temperature optima was the temperature at which the maximum initial velocity of uric acid production occurred and was used in determining the pH optima.

2. Determination of pH Optima.

The assay system was similar to that described under the previous Section. Here two buffer systems were used: 0.1 M pyrophosphate used over the pH range of 5 to 11 and 0.1 M Tris/HCl over the range of 7 to b 10. Variation in pH in both buffer systems was accomplished by titration of either the acid component with the base component or vice versa. The pH of solutions titrated was monitored constantly by an Orion Digital Ionanalyzer with accuracy of $\pm 0.001$ pH unit.

The reaction cuvette received 2.5 ml of the buffer (either pyrophosphate or Tris/HCl) and 25 microliters of 10 mM xanthine solution in 20 mM NaOH. The addition of the substrate did not change the pH of the system. The reaction was initiated by injection of 15 microliters of the enzyme preparation to be tested. Three replicates of each assay were performed and each series repeated every 0.1 pH unit. In the region of the optimum (or optima), the pH was varied 0.01 pH unit. The spectrophotometric conditions were held constant from one sample to the next or from one pH to the next. All assays were performed at 0.1 Absorbance full scale sensitivity at a chart speed of 5 cm/minute. The assay temperature was held constant at 22.25$\pm$0.02° C. (a value midway between the optima observed previously).

Figure 2:
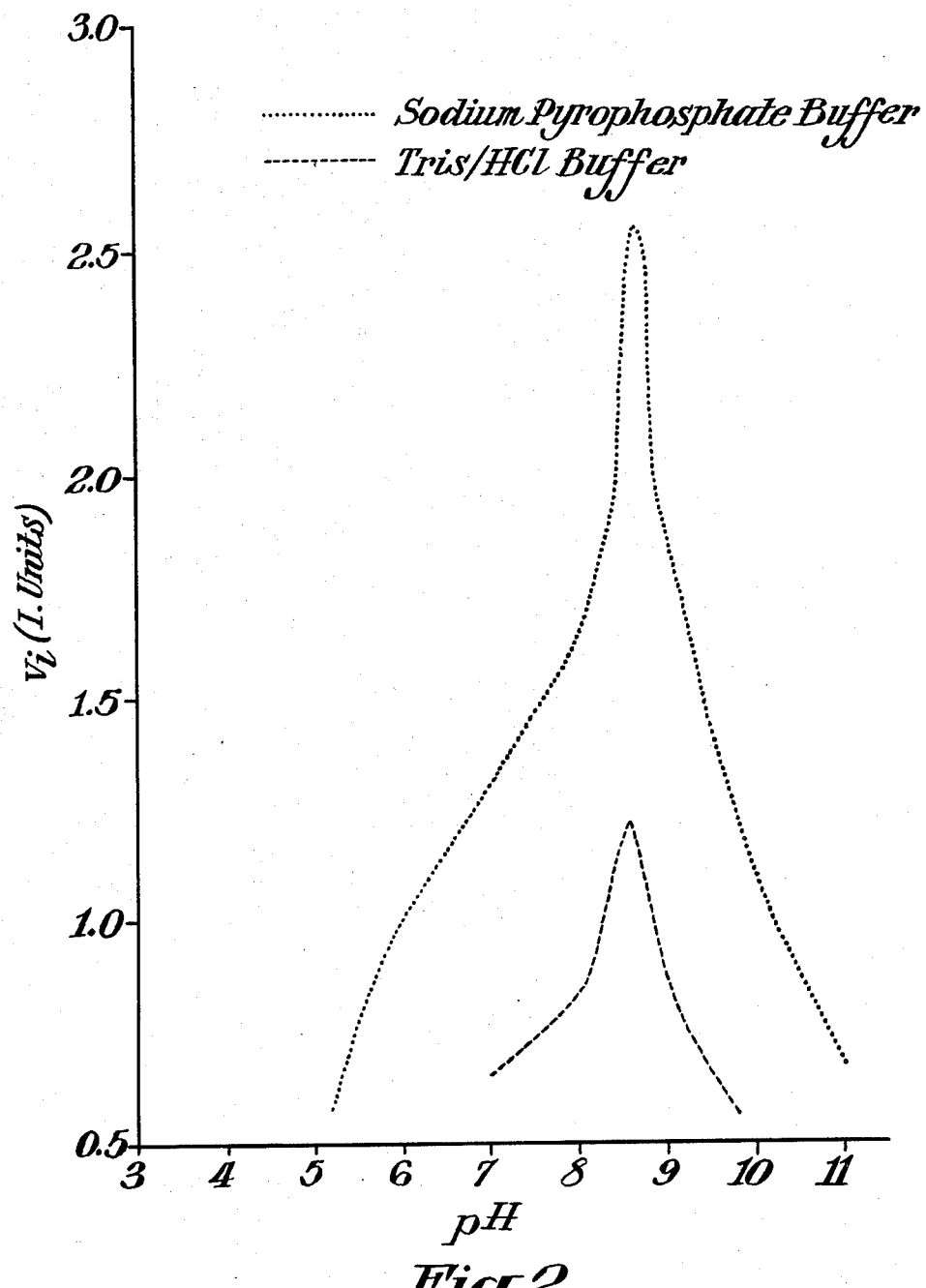

Initial velocities were determined from the slope of uric acid production curve within the first three minutes of the reaction. Plots were constructed of the change in initial velocity against change in pH. FIG. 1 is the pH profile for the XO concentrate of this invention. This profile contains data from the pyrophosphate and Tris/HCl buffer systems. FIG. 2 depicts the pH profile for XO prepared by prior art (Horecker and Heppel, 1955; Waud et al. 1975) again using the two buffer systems.

3. Determination of Michaelis Constants and Maximum Velocities Using Xanthine as Substrate.

XO concentrates of this invention when tested for pH profile showed the repeated occurrence of two pH peaks or optima, pH 8.3 and pH 8.7 (FIG. 1). XO concentrates prepared by prior art showed only one peak or optimum at pH 8.7 (FIG. 2). Because of this observation, the Michaelis constant (Km) determination with xanthine as a substrate was performed at pH 8.3 and pH 8.7 for all three XO preparations. Reaction mixtures contained 10 microliters of xanthine solution and 5 microliters of XO concentrate of this invention or XO concentrates prepared by the methods of prior art. The concentration of the substrate was varied over a gradient of initial concentrations of one to nine millimolar. Final substrate concentrations were determined by dividing the total reaction volume in microliters by the number of microliters of substrate used and then dividing the initial concentration of xanthine by this dilution factor. Since the pH 8.7 optimum was present in all the XO preparations using pyrophosphate buffer, the Km at this pH was determined first followed by determination of this constant at pH 8.3 for the three XO preparations. Three replicates of each assay were performed at each concentration of substrate. Buffer pH was monitored constantly and the percent oxygen saturation was maintained at approximately 75%. Lineweaver-Burk and Hanes plots were then constructed from the collected data. From these plots it was possible to obtain Km and maximum velocity (Vmax) for each of the XO preparations, which values are shown in Table 2.

4. Determination of Michaelis Constant and Maximum Velocity Using Hypoxanthine as Substrate.

An identical set of experiments was conducted using hypoxanthine as substrate. However, when equivalent concentration of this substrate was used as in the preceding experiments using xanthine ($10^{-5}$ M), it was observed that as the concentration of substrate was increased, enzyme activity decreased. To overcome this substrate inhibition, both enzyme and substrate concentrations were reduced. By reducing the final substrate concentration to $10^{-6}$ M and that of the enzyme to fivefold, it was possible to overcome this substrate's inhibition. Lineweaver-Burk and Hanes plots were constructed from the data and both Km and Vmax determined therefrom.

5. Inhibition of XO Activity by Folic Acid, Allopurinol, and Pterin-6-Carboxylic Acid.

Experimental conditions for this part of the study were similar to the preceding experiments. By varying the concentration of a given inhibitor while maintaining constant concentration of xanthine, it was possible to measure the inhibition constant ($K_I$) for each of the three inhibitors. From the collected data, Lineweaver-Burk plots for competitive inhibition were constructed. Information generated from these plots was used to construct replots which yielded the $K_I$ values directly from the intercepts which are included in Table 2.

vette contained 2.5 ml buffer, 25 μl of 10 mM xanthine, and 15 μl enzyme.

The pH profile curve of the XO concentrate of this invention with xanthine repeatedly revealed the presence of two closely associated peaks or optima (pH 8.3 and 8.7) at sub-saturating concentrations of substrate (FIG. 1). The pH profile of XO concentrate of the prior art repeatedly showed only a single optimum (pH 8.7) under the same experimental conditions (FIG. 2). This is a very significant difference and suggests that: (1) there is more than one ionic species on the active enzyme of the XO concentrate of this invention; (2) there is a functional group within the XO concentrate of this invention which is absent from the XO concentrates prepared by prior art; and (3) the chemical structure of XO prepared by prior art is different than the XO of the XO concentrates of this invention.

The effect of the presence of the pH 8.3 optimum corresponding to the functional group in the enzyme of the XO concentrate of this invention becomes very significant upon examination of the kinetic parameters for this and XO concentrates prepared by prior art. It will be noted from Table 2 that at pH 8.3 XO concentrate of this invention has a lower $K_m$ (the lower this value, the higher the affinity of the substrate for XO) for xanthine and 132% higher $V_{max}$ than XO concentrates as prepared by prior art. This indicates the XO concentrate of this invention is a superior preparation. At the same pH with hypoxanthine as substrate, Table 2 shows lower $K_m$ and higher $V_{max}$ values with XO concentrate of this invention. A similar trend is seen at pH 8.7 with xanthine and hypoxanthine giving again lower $K_m$ and higher $V_{max}$ with XO concentrate of this invention than

TABLE 2

Comparison of kinetic data for xanthine oxidase (XO) concentrates of the prior art and the new XO concentrate of this invention.

| Characteristic | XO by prior art[1] | XO by prior art[2] | XO of this invention |
|---|---|---|---|
| Temperature Optimum: | 21.75 ± 0.02° C. | 21.90 ± 0.02° C. | 22.75 ± 0.02° C. |
| pH Optimum: | 8.7 | 8.7 | 8.3 & 8.7 |
| $K_m$, $V_{max}$ with xanthine (pH 8.3): | | | |
| $K_m$ | $6.2 \times 10^{-5}$M | $6.0 \times 10^{-5}$M | $4.34 \times 10^{-5}$M |
| $V_{max}$ | 2.0 I.U. | 2.8 I.U. | 4.76 I.U. |
| $K_m$, $V_{max}$ with hypoxanthine (pH 8.3): | | | |
| $K_m$ | $1.28 \times 10^{-5}$M | $2.6 \times 10^{-5}$M | $6.9 \times 10^{-6}$M |
| $V_{max}$ | 1.25 I.U. | 1.31 I.U | 1.47 I.U. |
| $K_m$, $V_{max}$ with xanthine (pH 8.7): | | | |
| $K_m$ | $3.15 \times 10^{-5}$M | $3.01 \times 10^{-5}$M | $2.0 \times 10^{-5}$M |
| $V_{max}$ | 2.03 I.U. | 2.16 I.U. | 3.125 I.U. |
| $K_m$, $V_{max}$ with hypoxanthine (pH 8.7): | | | |
| $K_m$ | $1.84 \times 10^{-6}$M | $2.31 \times 10^{-6}$M | $2.8 \times 10^{-6}$M |
| $V_{max}$ | 0.448 I.U. | 0.463 I.U. | 0.666 I.U. |
| $K_I$ with folic acid (pH 8.7): | $1.79 \times 10^{-6}$M | $1.69 \times 10^{-6}$M | $1.15 \times 10^{-6}$M |
| $K_I$ with pterin-6-carboxylic acid (pH 8.7): | $1.5 \times 10^{-6}$M | $1.45 \times 10^{-6}$M | $1.0 \times 10^{-6}$M |

[1]Horecker, B. L. and Heppel, L. A. Methods in Enzymol. Vol. 2, 482-485 (1955).
[2]Waud, W. R., Brady, F. O., Willey, R. D., and Rajagopalan, K. V. Arch. Biochem. and Biophys.169:695-701 (1975).

The temperature optimum of the XO concentrate of this invention is higher than that of the prior art indicating that this XO concentrate has a higher heat stability than the XO concentrate of prior art.

FIG. 1 presents the pH profile for milk xanthine oxidase concentrate of this invention. The profile was conducted using two different buffer systems: 0.1 M pyrophosphate buffer and 0.1 M Tris/HCl buffer. The test cuvette contained 2.5 ml buffer, 25 μl of 10 mM xanthine, and 15 μl enzyme. FIG. 2 presents the pH profile for milk xanthine oxidase concentrate prepared by prior art (Horecker and Heppel, 1955; Waud et al. 1975), conducted by using two buffer systems. The test cuthat XO concentrates as prepared by prior art.

The comparative results indicate that some important chemical structural changes of XO may have occured during the purification procedures used by prior art. It is known that a molecule of XO is created from two 150,000 dalton polypeptide chains which eventually become subglobules and are held together by short segments of protein or "loops". It is believed that these "loops" are attacked by proteolytic enzymes and organic reagents used in isolation methods employed in prior art. If so, the reagents used in the preparation of the XO concentrate by prior art attack and remove these "loops" from XO and thus decrease its molecular weight, increase its electrophoresis mobility, change its chemical structure and kinetic characteristics, diminish its stability, and reduce its catalytic efficiency and hence may account for the differences as shown in Table 2. The inhibition constants ($K_I$) included in Table 2 also confirm the possibility that important changes take place on XO during the purification by methods used in prior art.

Milk xanthine oxidase is of great interest because of its complexity and catalytic versatility. The enzyme has low specificity for substrates and electron acceptors. It catalyses the oxidation of many purines, pteridines, aldehydes, and other heterocyclic compounds by a number of electron acceptors such as oxygen, NADH, dyes, ferricyanides, and cytochrome C (Avis et al., J. Chem. Soc. (London) Part I: 1212–1219, 1956; Corran et al., Biochem. J. 33:1694–1706, 1939; Murrey et al., J. Biol. Chem. 241:4798–4801, 1966). The presence of XO in excess or its absence, inhibition, or stimulation, reflects on the biochemistry of normal or abnormal cellular activity (Wyngaarden and Kelley, In The Metabolic Basis of Inherited Disease, 3rd Ed., McGraw-Hill Book Co., NY, NY, 1972). Although the primary pathway of uric acid production is known, the metabolic importance of XO is not fully understood. Recently it has been theorized that XO in bovine milk is a factor in the development of atherosclerosis in humans (Oster, Amer. J. Clin. Res. 2:30–35, 1971; In Myocardiology Vol. 1, pp. 803–813, University Park Press, Baltimore, MD, 1972; Ross et al., Proc. Soc. Exp. Biol. Med. 144:523–527, 1973). The new high purity XO enzyme concentrate of this invention should stimulate research in the above fields and lead to clinical and industrial applications.

It is apparent that changes and modifications may be made without departing from the invention in its broader aspects. The aim of the appended claims, therefore, is to cover all such changes and modifications as fall within the true spirit and scope of the invention.

I claim:

1. A milk xanthine oxidase active enzyme concentrate having an average protein to flavin ratio as measured by $E_{280nm}$ for protein and $E_{450nm}$ for flavin ranging from 2.0 to 4.1, one symmetric peak by ion-exchange gel chromatography, shows a single protein band by polyacrylamide disc gel electrophoresis, and has a pH profile curve at approximate optimum temperature of the change in initial velocity of uric acid productivity against change in pH that shows two peaks, one at pH of about 8.3 and the other at pH of about 8.7.

2. The xanthine oxidase enzyme concentrate of claim 1 characterized in that it has a Michaelis constant of about $4.34 \times 10^{-5}$ M and maximum velocity of about 4.76 I.U. with xanthine as substrate at a pH of 8.3 and a Michaelis constant of about $2.0 \times 10^{-5}$ M and maximum velocity of about 3.125 I.U. with xanthine as substrate at a pH of 8.7.

* * * * *